(12) United States Patent
Caputo et al.

(10) Patent No.: US 7,750,157 B2
(45) Date of Patent: Jul. 6, 2010

(54) LUMINESCENT COMPOUNDS HAVING A FUNCTIONALIZED LINKER ARM USED IN THE BIOCONJUGATION AND LABELING OF BIOMOLECULES

(75) Inventors: Giuseppe Caputo, Turin (IT); Roberto Gobetto, Gassino Torinese (IT); Guido Viscardi, Virle Piemonte (IT)

(73) Assignee: Universita' Degli Studi di Torino, Turin TO (IT)

( * ) Notice: Subject to any disclaimer, the term of this patent is extended or adjusted under 35 U.S.C. 154(b) by 678 days.

(21) Appl. No.: 11/628,226

(22) PCT Filed: Jun. 1, 2005

(86) PCT No.: PCT/IB2005/051782

§ 371 (c)(1),
(2), (4) Date: Jan. 8, 2007

(87) PCT Pub. No.: WO2005/119254

PCT Pub. Date: Dec. 15, 2005

(65) Prior Publication Data

US 2007/0231818 A1    Oct. 4, 2007

(30) Foreign Application Priority Data

Jun. 1, 2004    (IT)    ............ TO2004A0372

(51) Int. Cl.
*C07F 15/00* (2006.01)
*C12Q 1/00* (2006.01)

(52) U.S. Cl. ............... 546/2; 435/4; 435/7.1; 436/84; 436/537; 436/546; 436/800

(58) Field of Classification Search ........... 546/2; 436/84, 537, 546, 800; 435/4, 7.1
See application file for complete search history.

(56) References Cited

U.S. PATENT DOCUMENTS

| 4,745,076 A | 5/1988 | Mueller et al. |
| 5,221,605 A | 6/1993 | Bard et al. |
| 5,981,286 A | 11/1999 | Herrmann et al. |

FOREIGN PATENT DOCUMENTS

| EP | 0658564 A1 | 6/1995 |
| WO | WO 2005/119254 | 12/2005 |

OTHER PUBLICATIONS

Baker et al. "Iron complexes of pyridylimidazole derivatives" Aust. J. Chem. 30:771-780 (1977).
Charbonnière et al. "A comparison of the lability of mononuclear octahedral and dinuclear triple-helical complexes of cobalt(II)" J. Am. Chem. Soc. 119:2488-2496 (1997).
Charbonnière et al. "Structural, magnetic, and electrochemical properties of dinuclear triple helices: Comparison with their mononuclear analogues" Chem. Eur. J. 4:485-493 (1998).
Hopfgartner "Ion spray—Tandem mass spectrometry of supramolecular coordination complexes" J. Am. Soc. Mass Spectr. 5:748-756 (1994).
Telfer et al. "Thermal spin crossover in binuclear iron(II) helicates: Negative cooperativity and a mixed spin state in solution" Inorg. Chem. 40:4818-4820 (2001).
Torelli et al. "Ruthenium(II) as a novel labile partner in thermodynamic self-assembly of heterobimetallic d-f triple-stranded helicates" Chem. Eur. J. 10:3503-3516 (2004).
Int'l Search Report for PCT/IB2005/051782 mailed Nov. 28, 2005.

*Primary Examiner*—Charanjit S Aulakh
(74) *Attorney, Agent, or Firm*—Nixon & Vanderhye P.C.

(57) ABSTRACT

The present invention relates to luminescent compounds having a functionalised linker arm, their synthesis and use in bioconjugation and labelling of biomolecules, such as for example nucleosides, nucleotides, nucleic acids (DNA, RNA or PNA) and proteins, as well as their use in the execution of in vitro and in vivo analytic and diagnostic assays.

23 Claims, No Drawings

LUMINESCENT COMPOUNDS HAVING A FUNCTIONALIZED LINKER ARM USED IN THE BIOCONJUGATION AND LABELING OF BIOMOLECULES

This is a U.S. national-stage application of Intl Appln. No. PCT/IB2005/051782 under 35 U.S.C. 371, filed Jun. 1, 2005, designating the U.S. and published in English; the entire contents of which are hereby incorporated by reference in this application.

The present invention relates to luminescent compounds having functionalised linker arm, the synthesis and use thereof in the bioconjugation and labelling of biomolecules, such as for example nucleosides, nucleotides, nucleic acids (DNA, RNA or PNA) and proteins, as well as their use in the execution of in vitro and in vivo analytical and diagnostic assays.

There is a continuous and increasing need for highly specific and rapid methods for the detection and quantification of chemical, biochemical and biological substances. Methods for detecting and measuring small quantities of drugs, metabolites, micro-organisms and other diagnostically valuable materials, such as for example drugs for therapeutic use, hormones, pathogenic micro-organisms and viruses, tumour markers, antibodies, enzymes, nucleic acids, narcotics, poisons and abuse drugs are of particular interest. These materials are detected and assessed according to now well established techniques that exploit the high specificity binding between biochemical components, such as that found for example in the antigen-antibody, protein-ligand systems and in nucleic acid hybridisation. In these methods the presence of the diagnostically valuable component is typically detected by the presence or absence of a visualizable molecule, a so-called tracer, by means of a chemical-physical technique, such as for example detection of radioactivity, colour, luminescence, for example fluorescence, phosphorescence, chemiluminescence and electrochemiluminescence.

Electrochemiluminescence (ECL), or electro-generated chemiluminescence, consists of the production of light in the proximity of an electrode surface following the forming of species that can originate highly energetic electron transfer reactions.

ECL is therefore a means for converting electric energy into radiative energy and the process involves formation of excited electronic states as a result of electron transfer reactions between electrochemical-generated species.

ECL originates by annihilation in an electron transfer reaction between an oxidized and a reduced species, both generated at the electrode by alternating pulses of the potential.

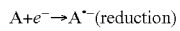A+e⁻→A·⁻(reduction)

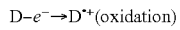D-e⁻→D·⁺(oxidation)

A·⁻+D·⁺→A*+D(excited state formation)

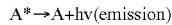A*→A+hv(emission)

The working electrode potential is rapidly oscillated between two potential values, so as to generate both the A·⁻ reduced species and the D·⁺ oxidized species, which will then react near the electrode surface to form the A* emitting state.

However, this type of reaction involves the use of non-aqueous solvents (for example dimethylformamide, acetonitrile) rigorously purified and deoxygenised, since the potential range available in water is too narrow to generate the required highly energetic precursors.

One-step ECL generation using a co-reagent capable of generating highly oxidizing or reducing species is of particular interest for practical applications.

For instance, in the $Ru(bpy)_3^{2+}/(CH_3CH_2CH_2)_3N$ system, ECL is produced following the simultaneous oxidation of $Ru(bpy)_3^{2+}$ and $(CH_3CH_2CH_2)_3N$:

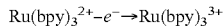Ru(bpy)₃²⁺-e⁻→Ru(bpy)₃³⁺

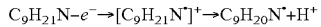C₉H₂₁N-e⁻→[C₉H₂₁N⁺]⁺→C₉H₂₀N·+H⁺

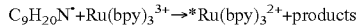C₉H₂₀N·+Ru(bpy)₃³⁺→*Ru(bpy)₃²⁺+products

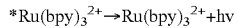*Ru(bpy)₃²⁺→Ru(bpy)₃²⁺+hv

This process involves the formation of a highly reducing species, $C_9H_{20}N·$, through an initial oxidation sequence.

The excited state that forms in the ECL reaction is the same that forms in a normal photo-excitation and therefore produces the same luminescence that is obtained from photo-luminescence spectroscopy.

The electrochemiluminescent reagent can be used to label biologically interesting molecules, such as DNA or antibodies, just like a photo-luminescent reagent. In contrast with fluorescence methods, however, ECL does not require the use of light excitation sources and therefore results as being immune from interference by luminescent impurities or diffused light.

ECL methods are of considerable interest for assessing many chemical and biological molecules, enabling highly sensitive, selective and high dynamic range analyses. In particular, ECL appears to be very promising for the commercial development of analytical methods for biological and diagnostically interesting molecules.

Electrochemiluminescent methods for assessing the presence of analytes of interest are preferable compared to the other methods because the background noise is reduced, due to the fact that in the biological samples there are not any species in turn electrochemiluminescent that can interfere with the analytical assay. In addition, the formation of the luminescent species in solution occurs electrochemically whereas detection occurs through optical means: the need to use optical filters in order to separate the excitation light from the emission light, as occurs usually in techniques using fluorescence, is thus eliminated. The most suitable chemical compounds used in analytical assays based on electrochemiluminescence are transition metal complexes, the ligands of which are generally bidentate. In chemistry, a complex is a structure composed of a core metal atom or ion surrounded by a number of negatively charged ions or neutral molecules that possess electronic doublets. A complex is also named coordination compound or metal complex. The ions or molecules that surround the metal are named ligands. Ligands are atoms or molecules capable of donating an electronic pair to the metal, usually through an available electronic doublet. Examples of ligands are chlorine, ammonia, water, pyridine, and the thiocyanate group. These types of ligands that form only one binding to the core atom are named monodentate. Ligands can also be molecules capable of occupying more than one coordination position in the same core metal, if in their structure they contain more than one atom capable of donating electronic doublets. In these cases reference is made to bidentate, tridentate, quadridentate, or, more generically, polydentate ligands.

ECL processes are known for many different molecules and particularly for transition metal complexes, such as ruthenium, osmium and rhenium. In order to be usable in analytical and biological assays, the complexes must contain functional groups that allow binding them, or conjugating them, to analytically interesting biological substances, such as antibodies, oligonucleotides, nucleotides, biotin, avidin, or to synthetic compounds usable in analytical assays. Functional groups useful for conjugation are localized on the metal ligands or at the end of a chain of atoms chemically bound to the ligand.

Transition metal complexes usable in analytical or bioanalytical assays are known in the art. For instance U.S. Pat. No. 5,221,605 (Bard and Whitesides) discloses ruthenium and osmium complexes having optionally substituted bipyridine, bipyrazine and phenantroline as the ligands, conjugated to biological substances. The patent EP0658564 (Massey et al.) discloses electrochemiluminescent ruthenium and osmium complexes, wherein the ligands are bipyridines, one of which is modified with a reactive group. The patent EP0178450 (Müller and Schmidt) discloses metal complexes having sulphonated or carboxylated bipyridine or phenantroline ligands, so as to increase their solubility in aqueous solutions. The U.S. Pat. No. 5,981,286 (Hermann et al.) discloses metal complexes containing hydrophilic bipyridine or phenantroline ligands.

An object of the present invention is to provide transition metal complex-type luminescent compounds provided with a linker arm suitable for the formation of a conjugate with a biomolecule, such as for example, nucleoside, nucleotide, nucleic acid or protein, or with a second compound capable of modifying the luminescent compound's chemical-physical, electrochemical and spectrochemical features or of forming a FRET pair.

This object is attained through a compound having the following general formula (I), including the valence tautomers thereof:

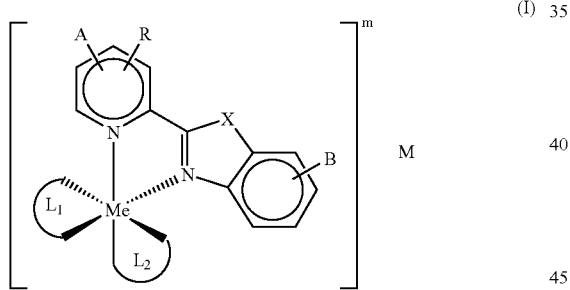

wherein:

Me is a transition metal or a rare earth metal;

R is a functional group selected from the group consisting of —COOH, —OH, —NH$_2$, or is —R$_{10}$—Y wherein R$_{10}$ is a saturated or unsaturated, linear or branched alkyl chain having from 1 to 30 carbon atoms, in which one or more carbon atoms are optionally each replaced by a heteroatom independently selected from oxygen and sulphur, or by a —NH— group, a —CONH— group, or an aromatic or non-aromatic, 4-, 5- or 6-membered cyclic grouping of carbon atoms, in which one or more carbon atoms are optionally each replaced by a heteroatom independently selected from oxygen, sulphur, nitrogen and selenium, and wherein Y is selected from the group consisting of hydrogen, carboxyl, carbonyl, amino, sulphidryl, thiocyanate, isothiocyanate, isocyanate, maleimide, hydroxyl, phosphoramidite, glycidyl, imidazolyl, carbamoyl, anhydride, bromoacetamido, chloracetamido, iodoacetamido, sulphonyl halide, acyl halide, aryl halide, hydrazide, N-hydroxysuccinimidyl ester, N-hydroxysulpho-succinimidyl ester, phtalimide ester, naphtalimide ester, monochlorotriazine, dichlorotriazine, mono- or di-halogen-substituted pyridine, mono- or di-halogen-substituted diazine, aziridine, imide ester, hydrazine, azidonitrophenyl, azide, 3-(2-pyridyldithio)-propionamide, glyoxal, aldehyde, —C≡CH and —COZ wherein Z is a leaving group;

A and B are independently of each other:

from zero to 4 substituents independently selected from the group consisting of hydrogen, —COOH, —OH, —NO$_2$, —OCH$_3$, —SO$_3$H, —SO$_3^-$, —R$_{11}$—Y', wherein R$_{11}$ is a saturated or unsaturated, linear or branched alkyl chain having from 1 to 30 carbon atoms, in which one or more carbon atoms are optionally each replaced by a heteroatom independently selected from oxygen and sulphur, or by a —NH— group, a —CONH— group, or an aromatic or non-aromatic, 4-, 5- or 6-membered cyclic grouping of carbon atoms, in which one or more carbon atoms are optionally each replaced by a heteroatom independently selected from oxygen, sulphur, nitrogen and selenium, and wherein Y' is selected from the group consisting of hydrogen, carboxyl, carbonyl, amino, sulphidryl, thiocyanate, isothiocyanate, isocyanate, maleimide, hydroxyl, phosphoramidite, glycidyl, imidazolyl, carbamoyl, anhydride, bromoacetamido, chloracetamido, iodoacetamido, sulphonyl halide, acyl halide, aryl halide, hydrazide, succinimidyl ester, hydroxysulphosuccinimidyl ester, phtalimide ester, naphtalimide ester, monochlorotriazine, dichlorotriazine, mono- or di-halogen-substituted pyridine, mono- or di-halogen-substituted diazine, aziridine, imide ester, hydrazine, azidonitrophenyl, azide, 3-(2-pyridyldithio)-propionamide, glyoxal, aldehyde, nitrophenyl, dinitrophenyl, trinitrophenyl, —C≡CH and aryl optionally substituted with one or more substituents independently selected from the group consisting of —SO$_3$H, carboxyl (—COOH), amino (—NH$_2$), carbonyl (—CHO), thiocyanate (—SCN), isothiocyanate (—CNS), epoxy and —COZ', wherein Y' and Z' have the meanings previously defined for R$_{10}$, Y and Z;

a 5- or 6-membered homocyclic or heterocyclic condensed ring optionally substituted with one to 4 substituents independently selected from the group consisting of hydrogen, —SO$_3^-$, —SO$_3$H, —COOH, —OH, —NO$_2$, —OCH$_3$, —NH$_2$, carbonyl (—CHO), thiocyanate (—SCN), isothiocyanate (—CNS), epoxy, —R$_{12}$—Y" and —COZ", wherein R$_{12}$, Y" and Z" have the meanings previously defined for R$_{10}$, Y and Z, respectively; or a homocyclic or heterocyclic condensed 2-fused-ring system, having 5 or 6 atoms in each ring, optionally substituted with one to 4 substituents selected from the group consisting of hydrogen, —SO$_3^-$, —SO$_3$H, —COOH, —OH, —NO$_2$, —OCH$_3$, —NH$_2$, carbonyl (—CHO), thiocyanate (—SCN), isothiocyanate (—CNS), epoxy, —R$_{13}$—Y''' and —COZ''', wherein R$_{10}$, Y''' and Z''' have the meanings previously defined for R$_{10}$, Y and Z, respectively;

X is selected from the group consisting of —O—, —S—, —Se—, —NH—, —C(CH$_3$)$_2$—, —NR$_{100}$— and

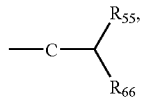

wherein $R_{100}$ is selected from the group consisting of hydrogen and $-R_{14}-Y''''$, wherein $R_{14}$ and $Y''''$ have the meaning previously defined for $R_{10}$ and Y, respectively, and $R_{55}$ and $R_{66}$ are independently of each other a saturated or unsaturated, linear or branched alkyl chain having from 1 to 30 carbon atoms, in which one or more carbon atoms are optionally each replaced by a heteroatom independently selected from oxygen and sulphur, or by a —NH— group, a —CONH— group, or an aromatic or non-aromatic, 4-, 5- or 6-membered cyclic grouping of carbon atoms, in which one or more carbon atoms are optionally each replaced by a heteroatom independently selected from oxygen, sulphur, nitrogen and selenium;

M is a counter ion; m is a number between −5 and +5;

$L_1$ and $L_2$ are independently of each other a bidentate ligand selected from the group consisting of:

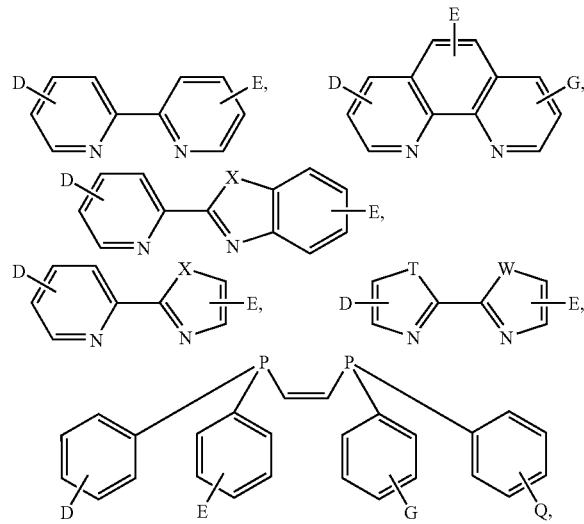

wherein D, E, G and Q have each independently the meanings previously defined for A and B, and T and W have each independently the meanings previously defined for X.

Preferably, the leaving groups Z, Z', Z'', Z''' and Z'''' are independently of each other selected from the group consisting of —Cl, —Br, —I, —OH, —$OR_{22}$, —$OCOR_{22}$, wherein $R_{22}$ is linear or branched $C_1$-$C_4$ alkyl (for example methyl, ethyl, t-butyl or i-propyl), —O—CO—Ar, wherein Ar is optionally substituted aryl, —O—CO-Het, wherein Het is a heterocyclic system preferably selected from succinimide, sulphosuccinimide, phtalimide and naphtalimide, —$NR_{33}R_{44}$, wherein $R_{33}$ and $R_{44}$ are each independently linear or branched $C_1$-$C_{10}$ alkyl.

The expression "carbon atom optionally replaced", as used above, indicates that such carbon atom may be replaced by one of the components or heteroatoms indicated above.

In the continuation of the description, the compounds of the present invention illustrated by formula (I) will be referred to as "ECL complexes".

The ECL complexes are luminescent complexes, that is to say complexes that are able to generate a detectable luminescent reaction. The luminescent reaction can be detected, for instance, by means of fluorescent or electrochemiluminescent measurements. In such complexes, the metal cation is a transition metal or a rare earth metal, preferably selected from the group consisting of Ru, Os, Re, Ir, Rh, Mo, Pt, Pd, In, Tc, Cu, W, Fe, Co, Va, Cr. Ruthenium, iridium, rhenium, chromium and osmium are particularly preferred.

The ECL complexes according to the present invention differ from the metal complexes known in the art in that they contain at least one ligand of the functionalised pyridylbenz-X-azolic type, in which X can be —O—, —S—, —Se—, —NH—, —C—, —C(CH_3)_2—, —NR_{100}— or

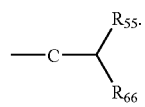

The pyridylbenz-X-azolic ligands are particularly advantageous compared to the previously mentioned known ligands since, by simply changing the X atom, a homologous series of ligands can be obtained which allow for modulation of the electrochemical and photophysical features of the complexes synthesized therewith. By using different pyridylbenz-X-azolic ligands it is therefore possible to synthesize transition metal complexes with different electrochemical and photophysical features and to use them in multiple analytical assays, that is to say assays in which each analyte is detected from a different complex.

Thus, advantageously, the present invention provides a homologous series of transition metal complex-type luminescent compounds containing at least one pyridylbenz-X-azolic type ligand, capable of emitting luminescence at different wavelengths, or characterized by different oxidation potentials, and also synthesizable by a method similar for all the elements of the series. The compounds of the present invention can therefore be used in multiple analytical assays, enabling the simultaneous detection of more analytes, each of them being conjugated with a different luminescent compound according to the invention.

The synthesis of the pyridylbenzoX-azolic ligand contemplates a two-step reaction, followed by the introduction of a functional group (R in formula (I)) containing a reactive group. Preferred reactive groups are active ester groups, such as N-hydroxysuccinimidyl ester, carboxylic acids, amino groups, thiols, maleimides, hydrazines. Optionally, besides the functional R group, additional functional groups can be added (A, B in formula (I)).

For successful functionalization, given the drastic reaction conditions in which one operates, it is necessary to protect the reactive group with a protective group that can easily be removed in conditions that do not compromise the structure of the complex itself. If the reactive group is a carboxylic acid, it has been established that the benzyl group is an excellent protective group that satisfies these requirements, which is removed by a basic hydrolysis.

The following steps can schematise the synthesis of ECL complexes of the present invention:

a) synthesis of the pyridylbenz-X-azolic ligand
b) synthesis of the intermediate $Me(L_1)(L_2)Cl_2$
c) synthesis of the $Me(L_1)(L_2)(benz-X-azolic\ ligand)]^m$ M complex The benz-X-azolic ligand can for example be synthesized starting from the 4-picoline according to the following scheme:

Scheme 1

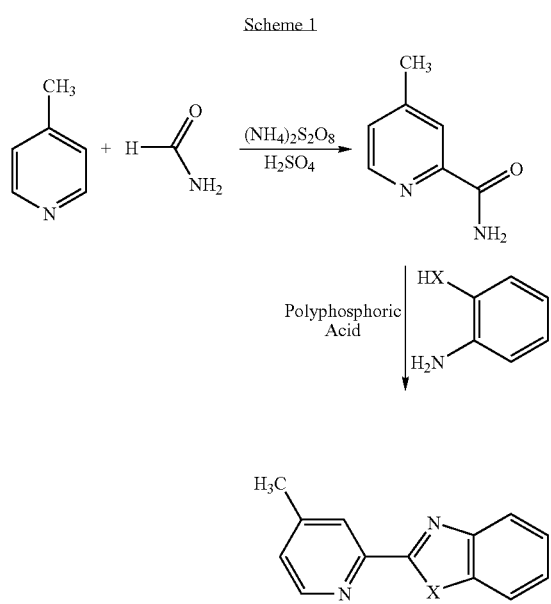

The functionalization of the ligand is carried out exploiting the reactivity of the picolinic methyl, the low acidity of which requires the use of strong bases, such as lithium diisopropylamide (LDA). The carbanion thus obtained is reacted with an alkyl bromide, adequately substituted with the reactive group that is to be introduced in the ligand, according to what is reported in Scheme 2. If an alkylcarboxylic acid is introduced, the use of LDA requires the protection of the carboxylic group as a benzyl ester, removable by a basic hydrolysis. The following scheme illustrates the introduction of a linker arm functionalised by a carboxylic acid.

Scheme 2

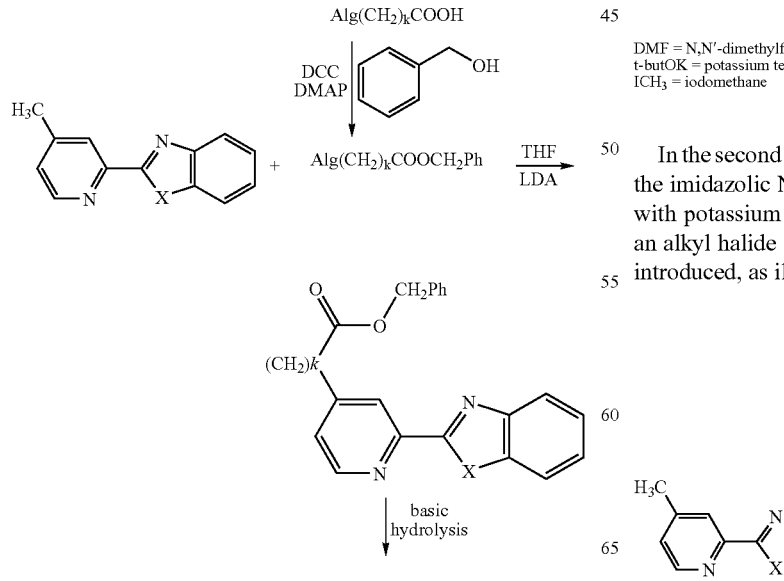

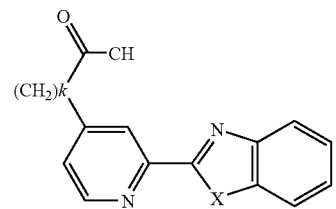

Alg = halogen
DCC = N,N'-dicycloesylcarbodiimide
DMAP = 4-dimethylaminopyridine
THF = tetrahydrofuran
LDA = lithium diisopropylamide
Ph = phenyl
k is a number between 1 and 30

When X in formula (I) is nitrogen, there are two possible ways to obtain the functionalised ligand. The first one passes through the quaternarization of one of the two imidazolic nitrogen atoms with an alkyl group (Scheme 3) and the subsequent functionalization through the picolinic methyl, as illustrated in Scheme 2.

Scheme 3

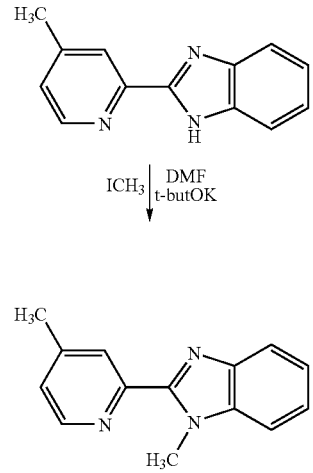

DMF = N,N'-dimethylformamide
t-butOK = potassium ter-buthyilate
ICH$_3$ = iodomethane In the second one, the ligand is selectively functionalised at the imidazolic NH group by deprotonation of the NH group with potassium tert-buthylate and subsequent reaction with an alkyl halide containing the functional group that is to be introduced, as illustrated in Scheme 4.

Scheme 4

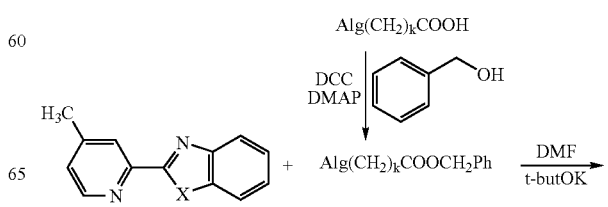

-continued

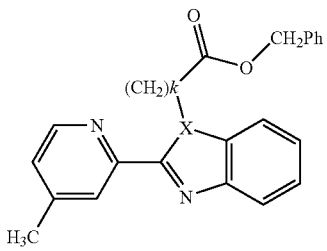

↓ basic hydrolysis

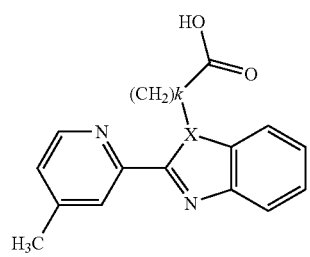

Alg = halogen
DCC = N,N'-dicyclohexylcarbodiimide
DMAP = 4-dimethylaminopyridine
DMF = N,N'-dimethylformamide
t-butOK = potassium ter-buthylate
Ph = phenyl
$k$ is a number between 1 and 30

The b) and c) steps are depicted in examples 1 to 4 and can be generalized for any $L_1$ and $L_2$ ligand. If $L_1$ and $L_2$ are two different ligands a chromatographic purification step will be necessary in order to obtain the desired compound.

Another object of the present invention is a conjugate of formula α-$ω_1$, wherein α is at least one ECL complex according to the present invention and $ω_1$ is a biological substance. Examples of biological substances that can be used are cells, viruses, proteins, lipoproteins, glycoproteins, peptides, polypeptides, nucleic acids, oligosaccharides, polysaccharides, lipopolysaccharides, cellular metabolites, hormones, pharmacologically active substances, alcaloids, steroids, vitamins, amino acids, sugars, antibodies, antigens, haptens and fragments thereof.

The ECL complex is preferably bound to the biological substance through a functional group of the complex itself, which can be covalently bound to a functional group present in the biological substance. If, for example, the functional group of the ECL complex is a reactive ester, it can react with a free amino group of the biomolecule. If, for example, the functional group of the ECL complex is a maleimide, it can react with a free SH group of the biological substance. Similarly, the functional groups of the biomolecule can be activated and consequently react with carboxylic acids, amino or thiol groups of the ECL complex. Preferred examples of biological substances are biotin, nucleic acids, antibodies or antibody fragments, antigens and haptens.

An α-$ω_2$ conjugate, wherein α is at least one ECL complex according to the present invention and $ω_2$ is a fluorescent dye conjugated to the ECL complex through a functional group of the latter, is also within the scope of the present invention. The fluorescent dye is a molecule capable of absorbing at wavelengths at which the ECL complex is able to emit, for instance a cyanine.

A specific non-limiting example of such a conjugate is 1-(4-sulphonatebuthyl)-1'-{Ru(II)[6-[(2-2'-bipyridine)$_2$ {2-[6-({[(2,5-dioxo-2,5-dihydro-1H-pyrrol-1-yl)penthyl] amino}sulphonyl)-3H-indol-2-yl]esanoylamino penthan}]}-1',3,3,3',3'-tetramethyl-5,5'-disulphonate indodicarbocyanine disodium salt:

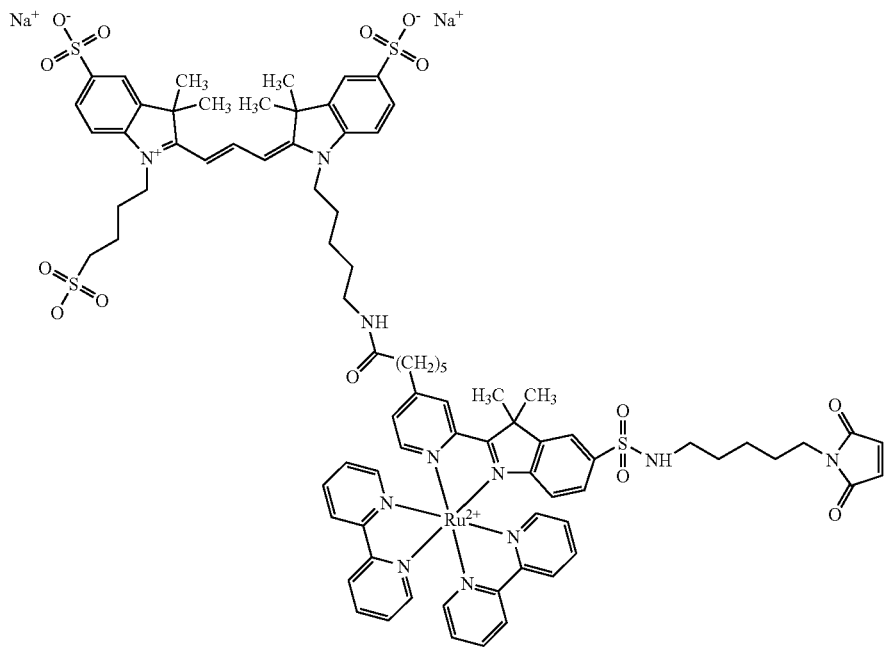

This conjugate is synthesized by reacting the ECL complex of the invention bis(2,2'-bipyridine) {2-[6-({[(2,5-dioxo-2,5-dihydro-1H-pyrrol-1-yl)penthyl]amino}sulphonyl)-3H-indol-2-yl]esanoic acid} ruthenium(II) with the 1-(4-sulphonatebuthyl)-1'-(5-aminopenthyl)-3,3,3',3'-tetramethyl-5,5'-disulphonate indodicarbocyanine disodium salt compound by a procedure similar to that of the Example 5, wherein BSA is replaced by the fluorophore.

Such a type of conjugate has very interesting optical properties that make it particularly useful as a tracer in bioanalytical applications. It can indeed be electrochemically excited by inducing the emission of the metal complex by electrochemiluminescence at about 630 nm. Such emission lies almost within the absorption maximum of the indodicarbocyanine bound to the complex that absorbs photons emitted by the complex and in turn becomes photoexcited, emitting fluorescence at 665 nm.

In addition, an $\alpha(\omega_1)(\omega_2)$-type conjugate, wherein $\alpha$ is at least one ECL complex according to the present invention, $\omega_1$ is a biological substance as defined above conjugated to the ECL complex through a first functional group, and $\omega_2$ is a fluorescent compound as defined above conjugated to the ECL complex through a second functional group, is also within the scope of the present invention. Such a conjugate can be obtained by reacting the $\alpha$-$\omega_2$ complex, as defined above, with a $\omega_1$ biomolecule, for instance bovine serum albumin (BSA), by a procedure similar to that depicted in Example 5.

A further object of the present invention is the use of a $\alpha$-$\omega_1$ or $\alpha(\omega_1)(\omega_2)$ conjugate in a method for qualitative and/or quantitative detection of an analyte in a sample to be tested. In this context the $\alpha$-$\omega_1$ or $\alpha(\omega_1)(\omega_2)$ conjugate of the present invention is used as a specific detectable reagent. The specificity of this reagent is brought about by the $\omega_1$ component, which is selected according to the analyte to be detected. On the contrary, the $\alpha$ component (ECL complex), optionally in combination with the $\omega_2$ fluorescent dye, represents the marker group, that is to say the analytical system component which is capable of generating a detectable signal. Preferably, the marker group is detected by electrochemiluminescence, in which case the luminescence is electrochemically generated at an electrode surface. Examples of electrochemiluminescent analytical assays in which metal complexes are used can be found in EP-A-0580979, WO 90/05301, WO 90/11511 and WO 92/14138. In addition, the marker group can be detected by fluorescence, in which case the ECL complex is excited by means of light radiation with an appropriate wavelength and the resulting fluorescence emission is measured. Examples of fluorescent analytical assays using transition metal complexes can be found in EP-A-0178450 and EP-A-0255534, that are incorporated herein as reference.

Another object of the present invention is an analytical method for the detection of an analyte in a sample, comprising the following steps:

(i) to contact the sample with a conjugate according to any one of claims 5, 6 or 10, in suitable conditions for the binding of the conjugate to the analyte, if present; and (ii) to assess the presence or the quantity of analyte bound to the conjugate in the sample by measuring the luminescence emitted by the conjugate bound to the analyte.

This method can also include a step in which the analyte is separated from the other sample components before the contact with the conjugate. In such a type of method, the $\alpha$-$\omega_1$ conjugate is for example a conjugate in which $\omega$1 is an antibody.

Furthermore, the method can comprise a step in which the analyte is separated from the other sample components by contacting with a second antibody attached to a solid phase.

A second example is the one in which the $\alpha$-$\omega_1$ conjugate is a conjugate wherein $\omega$1 is a DNA probe and the analyte is separated from the other sample components by contacting with a second DNA probe attached to a solid phase.

The examples that follow depict the synthesis of some preferred ECL complexes of the invention, the conjugation thereof with biological molecules (BSA, IgG), the spectroscopic and electrochemical characterization thereof and an analytical method using conjugates of ECL complexes with biological substances. Such examples are provided by way of illustration and are not intended to limit the scope of the invention, as defined in the appended claims.

EXAMPLE 1

Synthesis of [Ru(bpy)$_2$(LegN)](PF$_6$)$_2$

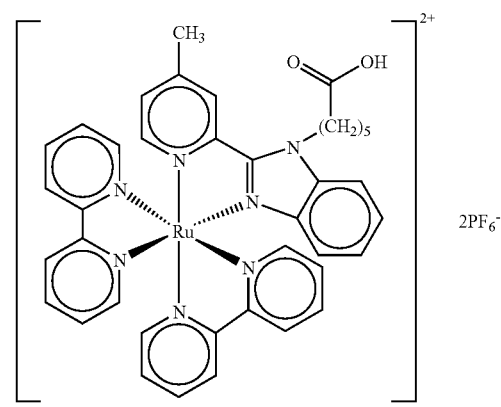

1a) Synthesis of [Ru(bpy)$_2$Cl$_2$]

1.50 g of RuCl$_3$.3H$_2$O (5.74·10$^{-3}$ mol), 1.8 g of 2,2'-bipyridine (1.15·10$^{-2}$ mol) and 1.7 g of LiCl are dissolved in 50 ml of N,N-dimethylformamide. The mixture is degassed under Ar for 15 minutes and then refluxed for 7 hours. After cooling at room temperature, the solution is poured into 200 ml of acetone with rapid stirrING. The solution is then kept overnight at 0° C. The microcrystalline precipitate formed is filtered, washed with 75 ml of water and 75 ml of ethyl ether. 1.60 g of [Ru(bpy)$_2$Cl$_2$].2H$_2$O are obtained, with a yield of 54%.

1b) Synthesis of 6-bromo-hexanoic acid benzyl ester

A mixture of 6-bromo-hexanoic acid (0.10 mol), benzyl alcohol (0.10 mol), 4-dimethylaminopyridine (1.78·10$^{-2}$ mol) and dichloromethane (600 ml) is stirred and kept at 0° C. with an ice bath, then added with N,N'-dicyclohexylcarbodiimide (0.13 mol) and left to react for 16 hours. At the end of the reaction, the solution is filtered and the precipitate is discarded, whilst the solution is repeatedly washed with H$_2$O, discarding the precipitate possibly formed. The organic layers are pooled and washed again with a saturated solution of NaHCO$_3$, a solution of HCl 0.1 M and then with water. The solution is dried with MgSO$_4$, filtered, and the solvent is removed by vacuum evaporation.

Purification with Flash chromatography, elution with a mixture of petroleum ether/ethyl acetate. An oily liquid is obtained with a yield of 93%.

1c) Synthesis of benzyl 6-[2-(4-methylpyridin-2-yl)-benzoimidazol-1-yl)hexanoic acid (LegN-benz)

450 g of polyphosphoric acid, 40 g (0.29 mol) of 4-methyl-pyridine-2-carboxylic acid amide and 31 g (0.29 mol) of o-phenylendiamine are added in a three-neck round-bottom flask, equipped with a condenser, a thermometer and mechanical stirring. The mixture is heated at 210° C. for 4 hours. At the end, the mixture is cooled at 70° C. and the crude is added to 1 L of water. Basify with a 50% aqueous solution of sodium hydroxide and filter the solid obtained. Crystallize from absolute ethanol. The product 2-(4-methylpyridin-2-yl)-1H-benzoimidazol is obtained with a yield of 85%. Melting point: 228-9° C.

10 g (0.048 mol) of the compound 2-(4-methylpyridin-2-yl)-1H-benzoimidazole synthesised in the previous step, are dissolved in 100 ml of anhydrous dimethyformamide at room temperature in a 250 ml three-neck round-bottom flask and 6.3 g (0.056 mol) of freshly sublimated potassium tert-butylate are added. After 15 min of stirring, 46 g (0.16 mol) of 6-bromo-hexanoic acid benzyl ester are added dropwise and heated at 45° C. for 15 hours. After cooling, 100 ml of deionised water are added and the mixture is extracted with ethyl acetate. After drying of the organic layers with anhydrous sodium sulphate, the solvent is removed by evaporation under vacuum and the crude product is purified by Flash chromatography over a silica gel column, eluting with a gradient starting from a mixture of petroleum ether/ethyl acetate (95:5) and ending with a mixture of petroleum ether/ethyl acetate (70:30). A slightly yellow oil is obtained with a yield of 75%.

1d) Synthesis of [Ru(bpy)$_2$(LegN)](PF$_6$)$_2$ 7.69·10$^{-4}$ mol of [Ru(bpy)$_2$Cl$_2$].2H$_2$O and 1.15·10$^{-3}$ mol of LegN-benz are dissolved in 50 ml of ethylene glycol in a flask. The mixture is degassed with Ar for 15 minutes and then refluxed for 4 hours. After cooling at room temperature, 20 ml of water and 10 ml of an aqueous solution of NH$_4$PF$_6$ are added. The precipitate formed is collected and recrystallized in 1:1 acetonitrile/ethanol mixture. 0.293 g of [Ru(bpy)$_2$(LegN-benz)](PF$_6$)$_2$ are obtained with a yield of 80%. The complex is then dissolved in 80 ml of a 10% solution of KOH in methanol and the mixture is stirred at room temperature for at least 15 hours. After acidification at pH≈1-3 with H$_2$SO$_4$, methanol is removed by vacuum evaporation and the acidic solution is extracted with dichloromethane. The organic fractions are pooled, dehydrated with Na$_2$SO$_4$, and the solvent is removed by vacuum evaporation. The product [Ru(bpy)$_2$(LegN)](PF$_6$)$_2$ is obtained.

EXAMPLE 2

Synthesis of [Ru(bpy)$_2$(LegO)](PF$_6$)$_2$

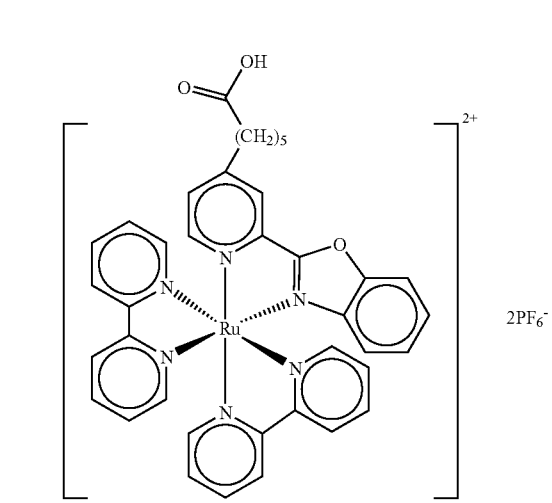

2a) Synthesis of [Ru(bpy)$_2$Cl$_2$]

The intermediate [Ru(bpy)$_2$Cl$_2$] is synthesized as in example 1a).

2b) Synthesis of 6-bromo-hexanoic acid benzyl ester

The ligand is synthesised as in step 1b).

2c) Synthesis of 6-(2-(benzoxazol-2-yl-pyridin-4-yl) hexanoic acid benzyl ester(LegO-benz)

Polyphosphoric acid (220 ml), 4-methyl-pyridine-2-carboxylic acid amide (0.29 mol) and o-aminophenol (0.29 mol) are added in a three-neck round-bottom flask, equipped with a condenser, a thermometer and mechanical stirring. The mixture is reacted at 210° C. for 4 hours, then the solution is percolated in H$_2$O. The precipitate is filtered and suspended in a saturated aqueous solution of NaHCO$_3$. The precipitate is filtered again and washed with H$_2$O. The product 2-(4-methyl-pyridin-2-yl)-benzothiazole is crystallized from cyclohexane after having filtered and eliminated insoluble impurities.

Then a mixture of THF (~90 ml) and diisopropylamine (1 equivalent) is charged in a three-neck round-bottom flask, stirred and cooled at −78° C.; then a butyllitium solution (n-BuLi, 1.7 M in hexane, 1.1 equivalents) is added. The solution is stirred at −78° C. for 10 minutes, warmed up at 0° C. and stirred for 10 min, and again cooled at −78° C.

A solution of anhydrified 2-(4-methyl-pyridin-2-yl)-benzooxazol (1 equivalent) is cannuled in THF and the mixture is stirred for 1 hour at −78° C., then the benzyl ester of anhydrified 6-bromo-hexanoic acid (1.1 equivalents) is added by a syringe and reacted for a minimum of 3 hours at room temperature. The reaction is stopped with ice and NH$_4$Cl and the solution is extracted with ethyl acetate. The organic layers are pooled and anhydrified with Na$_2$SO$_4$ and the solvent is removed by vacuum evaporation. Purification is carried out by Flash chromatography with gradient elution of a mixture of dichloromethane/methanol. A slightly yellow solid was obtained.

2d) Synthesis of [Ru(bpy)$_2$(LegO)](PF$_6$)$_2$ 0.200 g of [Ru(bpy)$_2$Cl$_2$].2H$_2$O (3.84·10$^{-4}$ mol) and 0.120 g of (4-methyl-2-pyiridyl)benzoxazol (5.71·10$^{-3}$ mol) are dissolved in 50 ml of ethylene glycol. The mixture is degassed with Ar for 15 minutes and then refluxed for 4 hours. The initially violet solution progressively changes to a clearer, reddish solution in about one hour and after 4 hours its colour is definitively red.

After cooling at room temperature, 20 ml of water and 10 ml of an aqueous solution of NH$_4$PF$_6$ (1.0 g/10 ml) are added.

The precipitate formed is then collected, washed with 10 ml of H$_2$O and dried with Et$_2$O.

0.275 g of [Ru(bpy)$_2$(LegO-benz)](PF$_6$)$_2$ are obtained, with a yield of 78.4%. The complex is dissolved in 80 ml of a 10% solution of KOH in methanol and then stirred for at least 15 hours at room temperature. After acidification at pH≈2-3, the methanol is removed by evaporation at reduced pressure, and the acidic solution is extracted with dichloromethane.

All the organic fractions are pooled, dehydrated with Na$_2$SO$_4$ and the solvent is removed by evaporation at reduced pressure.

The product [Ru(bpy)$_2$(LegO)](PF$_6$)$_2$ is obtained.

EXAMPLE 3

Synthesis of [Ru(bpy)$_2$(LegS)](PF$_6$)$_2$

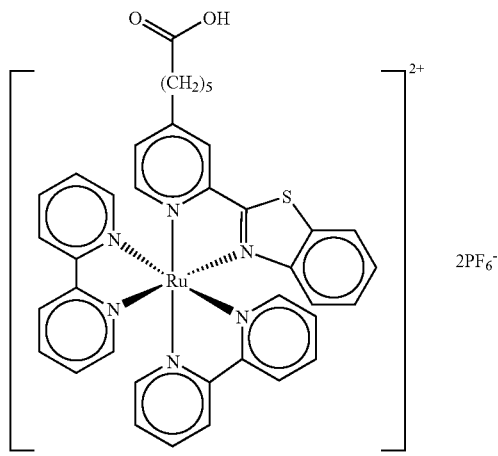

3a) Synthesis of [Ru(bpy)$_2$Cl$_2$]

The intermediate [Ru(bpy)$_2$Cl$_2$] is synthesized as in example 1a).

3b) Synthesis of 6-bromo-hexanoic acid benzyl ester

The compound is synthesised as in step 1b).

3c) Synthesis of 6-(2-(benzothiazol-2-yl-pyridin-4-yl)hexanoic acid benzyl ester (LegS-benz)

Polyphosphoric acid (220 ml), 4-methyl-pyridine-2-carboxylic acid amide (0.29 mol) and o-aminothiophenol (0.29 mol) are added in a three-neck round-bottom flask, equipped with a condenser, a thermometer and mechanical stirring.

The mixture is reacted at 210° C. for 4 hours, then the solution is percolated in H$_2$O. The precipitate is filtered and suspended in a saturated aqueous solution of NaHCO$_3$.

The solution is filtered again and the precipitate is washed with H$_2$O. The product 2-(4-methyl-pyridin-2-yl)-benzothiazole is crystallised from cyclohexane after having filtered and eliminated the insoluble impurities.

Then a mixture of THF (~90 ml) and diisopropylamine (1 equivalent) is charged in a three-neck round-bottom flask, stirred and cooled at −78° C.; then a butyllitium solution (n-BuLi, 1.7 M in hexane, 1.1 equivalents) is added. The solution is stirred at −78° C. for 10 minutes, warmed up at 0° C. and stirred for 10 min, and again cooled at −78° C.

A solution of anhydrified 2-(4-methyl-pyridin-2-yl)-benzothiazole (1 equivalent) is cannuled in THF and the mixture is stirred for 1 hour at −78° C., then the benzyl ester of anhydrified 6-bromo-hexanoic acid (1.1 equivalents) is rapidly added by a syringe and reacted for a minimum of 3 hours at room temperature.

The reaction is stopped with ice and NH$_4$Cl and the solution is extracted with ethyl acetate. The organic layers are pooled and anhydrified with Na$_2$SO$_4$ and the solvent is removed by vacuum evaporation.

Purification is carried out by Flash chromatography with gradient elution of a mixture of petroleum ester/ethyl acetate. A grey solid is obtained.

3d) Synthesis of [Ru(bpy)$_2$(LegS)](PF$_6$)$_2$ 3.84·10$^{-4}$ mol of [Ru(bpy)$_2$Cl$_2$].2H$_2$O and 5.74·10$^{-4}$ mol of LegS-benz are dissolved in 50 ml of ethylene glycol. The mixture is degassed with Ar for 15 minutes and then refluxed for 4 hours.

The solution, initially violet, progressively changes to a clearer, reddish solution in about one hour and after 4 hours its colour is definitively red.

After cooling at room temperature, 20 ml of water and 10 ml of an aqueous solution of NH$_4$PF$_6$ (1.0 g/10 ml) are added. The precipitate formed is then collected, washed with 10 ml of water and dried with Et$_2$O. 0.298 g of [Ru(bpy)$_2$(LegS-benz)](PF$_6$)$_2$ are obtained with a yield of 83.5%. The complex is dissolved in 80 ml of a 10% solution of KOH in methanol and then stirred for at least 15 hours at room temperature.

After acidification at pH≈2-3 with H$_2$SO$_4$, the methanol is removed by evaporation at reduced pressure, and the acidic solution is extracted with dichloromethane.

The organic fractions are pooled, dehydrated with Na$_2$SO$_4$ and the solvent is removed by evaporation at reduced pressure. The product [Ru(bpy)$_2$(LegS)](PF$_6$)$_2$ is obtained.

EXAMPLE 4

Synthesis of [Ru(bpy)$_2$(LegC)](PF$_6$)$_2$

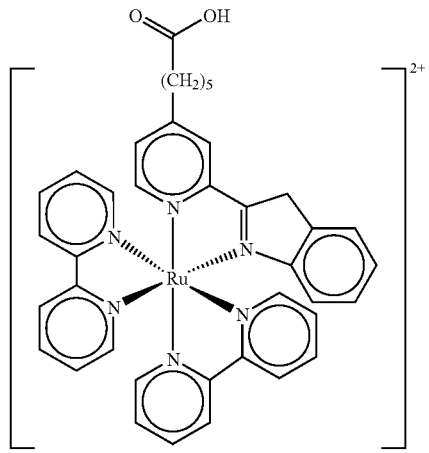

4a) Synthesis of [Ru(bpy)$_2$Cl$_2$]

The intermediate [Ru(bpy)$_2$Cl$_2$] is synthesized as in example 1a).

4b) Synthesis of 6-bromo-hexanoic acid benzyl ester

The compound is synthesised as in step 1b).

4c) Synthesis of 6-(2-(3H-indol-2-yl)pyridin-4-yl) hexanoic acid benzyl ester (LegC-benz)

Polyphosphoric acid (220 ml), 4-methyl-pyridine-2-carboxylic acid amide (0.29 mol) and 2-aminobenzonitrile (0.29 mol) are added in a three-neck round-bottom flask, equipped with a condenser, a thermometer and mechanical stirring. The mixture is reacted at 210° C. for 4 hours, then the solution is percolated in H$_2$O. The precipitate is filtered and suspended in a saturated aqueous solution of NaHCO$_3$. The solution is filtered again and the precipitate is washed with H$_2$O. The product 2-(4-methyl-pyridin-2-yl)-3H-indole is crystallised from cyclohexane after having filtered and eliminated the insoluble impurities.

Then a mixture of THF (~90 ml) and diisopropylamine (1 equivalent) is charged in a three-neck round-bottom flask, stirred and cooled at −78° C.; then a butyllitium solution (n-BuLi, 1.7 M in hexane, 1.1 equivalents) is added. The solution is stirred at −78° C. for 10 minutes, warmed up at 0° C. and stirred for 10 min, and again cooled at −78° C.

A solution of anhydrified 2-(4-methyl-pyridin-2-yl)-3H-indole (1 equivalent) is cannuled in THF and the mixture is stirred for 1 hour at −78° C., then the benzyl ester of anhydrified 6-bromo-hexanoic acid (1.1 equivalents) is rapidly added by a syringe and reacted for a minimum of 3 hours at room temperature.

The reaction is stopped with ice and NH$_4$Cl and the solution is extracted with ethyl acetate. The organic layers are pooled and anhydrified with Na$_2$SO$_4$ and the solvent is removed by vacuum evaporation.

Purification is carried out by Flash chromatography with gradient elution of a mixture of petroleum ester/ethyl acetate. A slightly yellow solid is obtained.

4d) Synthesis of [Ru(bpy)$_2$(LegC)](PF$_6$)$_2$ $3.84 \cdot 10^{-4}$ mol of [Ru(bpy)$_2$Cl$_2$].2H$_2$O and $5.74 \cdot 10^{-4}$ mol of LegC-benz are dissolved in 50 ml of ethylene glycol. The mixture is degassed with Ar for 15 minutes and then refluxed for 4 hours. The solution, initially violet, progressively changes to a clearer, reddish solution in about one hour and after 4 hours its colour is definitively red.

After cooling at room temperature, 20 ml of water and 10 ml of an aqueous solution of NH$_4$PF$_6$ (1.0 g/10 ml) are added. The precipitate formed is then collected, washed with 10 ml of water and dried with Et$_2$O. 0.304 g of [Ru(bpy)$_2$(LegC-benz)](PF$_6$)$_2$ are obtained, with a yield of 84%. The complex formed is dissolved in 80 ml of a 10% solution of KOH in methanol and then stirred for at least 15 hours at room temperature. After acidification at pH≈2-3 with H$_2$SO$_4$, the methanol is removed by evaporation at reduced pressure, and the acidic solution is extracted with dichloromethane. The organic fractions are pooled, dehydrated with Na$_2$SO$_4$ and the solvent is removed by evaporation at reduced pressure. The product [Ru(bpy)$_2$(LegC)](PF$_6$)$_2$ is obtained.

EXAMPLE 5

Conjugation of [Ru(bpy)$_2$(LegN)](PF$_6$)$_2$ with BSA $1.34 \cdot 10^{-5}$ mol of [Ru(bpy)$_2$LegN](PF$_6$)$_2$, $2.68 \cdot 10^{-5}$ mol of dicyclohexylcarbodiimide (DCC) and $2.68 \cdot 10^{-5}$ mol of N-hydroxysuccinimide (NHS) are dissolved in a round-bottom flask containing 5 ml of anhydrous DMF. The solution is reacted for 5 hours at 70° C. over a silicon oil bath. The N-hydroxysuccinimide ester of the complex [Ru(bpy)$_2$LegN](PF$_6$)$_2$ is obtained After 5 hours, 56 µl are drawn from the ester solution (1.50 $10^{-7}$ mol) and 1 ml (1.50 $10^{-8}$ mol) of a 1 mg/ml BSA solution in sodium borate buffer (pH 8.5) are added, so that the molar ratio between [Ru(bpy)$_2$LegN-NHS)](PF$_6$)$_2$ and BSA is 10:1. The two portions are pooled and reacted for 2 hours at room temperature. After 2 hours, a second portion of 56 µl of [Ru(bpy)$_2$LegN-NHS)](PF$_6$)$_2$ is added and the reaction continued for another 2 hours. The conjugate {[Ru(bpy)$_2$(LegN)]-BSA} obtained is purified over a chromatographic column PD10 type, containing a Sephadex GD25 resin, eluting with sodium borate buffer pH 8.5. The 1 ml fractions are collected in Eppendorf tubes.

EXAMPLE 6

Conjugation of [Ru(bpy)$_2$(LegS)](PF$_6$)$_2$ with IgG (Immunoglobulin G)

$1.34 \cdot 10^{-5}$ mol of [Ru(bpy)$_2$LegS](PF$_6$)$_2$, $2.68 \cdot 10^{-5}$ mol of dicyclohexylcarbodiimide (DCC) and $2.68 \cdot 10^{-5}$ mol of N-hydroxysuccinimide (NHS) are dissolved in a round-bottom flask containing 5 ml of anhydrous DMF. The mixture is reacted for 5 hours at 70° C. over a silicon oil bath.

After 5 hours, 56 µl are drawn from the ester solution (1.50 $10^{-7}$ mol) and 1 ml (1.50 $10^{-8}$ mol) of a 2.33 mg/ml solution of IgG in 1 ml sodium borate buffer (pH 8.5) are added, so that the molar ratio between [Ru(bpy)$_2$LegS-NHS](PF$_6$)$_2$ and IgG is 10:1. The two portions are pooled and reacted for 2 hours of stirring at room temperature. After 2 hours, a second 56 µl portion of [Ru(bpy)$_2$LegS-NHS](PF$_6$)$_2$ is added and the reaction continued for another 2 hours. The conjugate {[Ru(bpy)$_2$(LegS)]-IgG} obtained is purified over a chromatographic column PD10 type, containing a Sephadex GD25 resin, eluting with sodium borate buffer pH 8.5. The 1 ml fractions are collected in Eppendorf tubes.

EXAMPLE 7

Spectroscopic and Electrochemical Characterization

The complexes [Ru(bpy)$_2$(LegN)](PF$_6$)$_2$, [Ru(bpy)$_2$(LegO)](PF$_6$)$_2$, [Ru(bpy)$_2$(LegS)](PF$_6$)$_2$ and [Ru(bpy)$_2$(LegC)](PF$_6$)$_2$ have been characterized by spectroscopic and electrochemical point of view.

Electrochemical characterization has been carried out by means of cyclic voltammetry measurements; tests have been made in dichlorometane, using tetrabutylammonium hexafluorophosphate as support electrolyte. The working electrode is made of glassy carbon (CG), the auxiliary of Pt, while the reference electrode is a normal SCE (Saturated Calomel Electrode). The potentials are reported with respect to the ferrocene redox couple Fc/Fc$^+$ which in the experimental conditions used shows a half-wave potential $E_{1/2}$=+0.46 V.

Resistance compensation has been carried out by means of positive feedback method. In the range 50 mV-3 V/s $\Delta E_p$ remains in the order of 60 mV, while peak currents $i_p$ are directly proportional to the square root of the scanning rate. Experiments have been carried out dissolving the ECL complexes in acetonitrile and using tetrabutylammonium hexafluorophosphate as support electrolyte.

The electrochemical behaviour of the complex $[Ru(bpy)_2(LegN)](PF_6)_2$ is characterized by two monoelectronic reductions and one monoelectronic oxidation, chemically and electrochemically reversible. The two reduction processes are characterized by a half-wave potential of $-1.764$ V and $-2.018$ V respectively, while the oxidation process shows a potential $E_{1/2}=0.793$ V.

The electrochemical behaviour of the complex $[Ru(bpy)_2(LegO)](PF_6)_2$, is characterized by two reversible monoelectronic reductions and one reversible monoelectronic oxidation. The two reduction processes are characterized by a half-wave potential of $-1.563$ V and $-1.924$ V respectively, while the oxidation process shows a potential $E_{1/2}=1.010$ V.

Also the electrochemical behaviour of the complex $[Ru(bpy)_2(LegS)](PF_6)_2$ is characterized by two monoelectronic reductions and one monoelectronic oxidation, chemically and electrochemically reversible. The two reduction processes are characterized by a half-wave potential of $-1.487$ V and $-1.914$ V respectively, while the oxidation process shows a potential $E_{1/2}=1.008$ V.

Analogously the electrochemical behaviour of the complex $[Ru(bpy)_2(LegC)](PF_6)_2$ is characterized by two reversible monoelectronic reductions and one reversible monoelectronic oxidation. The two reduction processes are characterized by a half-wave potential of $-1.650$ V and $-1.976$ V respectively, while the oxidation process shows a potential $E_{1/2}=0.915$ V.

In the following Table 1 are summarized the relevant data for the four complexes used as representative examples:

TABLE 1

| Complexes | Parameters | | | | |
|---|---|---|---|---|---|
| | $E_{1/2}$ Ox | $E_{1/2}$ Red1 | $E_{1/2}$ Red2 | Abs MLCT Band | Em |
| $[Ru(bpy)_2(LegC)](PF_6)_2$ | 0.915 V | $-1.650$ V | $-1.976$ V | 450 nm | 622 nm |
| $[Ru(bpy)_2(LegN)](PF_6)_2$ | 0.793 V | $-1.764$ V | $-2.018$ V | 460 nm | 632 nm |
| $[Ru(bpy)_2(LegO)](PF_6)_2$ | 1.010 V | $-1.563$ V | $-1.924$ V | 450 nm | 666 nm |
| $[Ru(bpy)_2(LegS)](PF_6)_2$ | 1.008 V | $-1.487$ V | $-1.914$ V | 450 nm | 684 nm |

EXAMPLE 8

Electrochemiluminescent Detection of $\{[Ru(bpy)_2(LegN)]\text{-}BSA\}(PF_6)_2$ Conjugate The conjugate $\{[Ru(bpy)_2(LegN)]\text{-}BSA\}(PF_6)_2$ made in Example 5 has been dissolved in PBS buffer to obtain four solutions with molar concentration equal to $10^{-11}$, $10^{-10}$, $10^{-9}$, $10^{-8}$. The experiments have been carried out in the electrochemical cell used in the cyclic voltammetry measurements described in Example 7. Emitted luminescence has been recorded with a Hamamatsu R928 photomultiplier tube connected to a computer equipped with a data acquisition board. Table 2 summarizes the results obtained with different conjugate solutions. PBS buffer only has been used as blanc.

TABLE 2

| Concentration | Emission Intensity (arbitrary units) |
|---|---|
| 0 | 32.53 |
| $10^{-11}$ M | 68.25 |
| $10^{-10}$ M | 109.63 |
| $10^{-9}$ M | 201.22 |
| $10^{-8}$ M | 598.12 |

EXAMPLE 9

Simultaneous Detection of the Conjugates $\{[Ru(bpy)_2(LegN)]\text{-}BSA\}(PF_6)_2 e\{[Ru(bpy)_2(LegS)]\text{-}IgG\}(PF_6)_2$ Analogously to the previous example four solutions of molar concentration equal to $10^{-11}$, $10^{-10}$, $10^{-9}$, and $10^{-8}$ of the conjugates $\{[Ru(bpy)_2(LegN)]\text{-}BSA\}(PF_6)_2 e\{[Ru(bpy)_2(LegS)]\text{-}IgG\}(PF_6)_2$, synthesized in Example 5 and Example 6 respectively, have been prepared. The experiments have been carried out in the electrochemical cell used in the cyclic voltammetry measurements described in Example 7. Emitted luminescence has been recorded with two Hamamatsu R928 photomultiplier tube connected to an oscilloscope connected to a computer equipped with a data acquisition board.

The first photomultiplier tube is equipped with a bandpass optical filter XF3028 (630±30 nm) centred at 630 nm, the second is equipped with a bandpass optical filter XF3031 (682±22 nm) centred at 682 nm.

Table 3 summarizes the electrochemiluminescent emissions detected with different conjugate solutions. PBS buffer only has been used as blanc.

TABLE 3

| Solution Concentration | Emission Intensity (arbitrary units) $\{[Ru(bpy)_2(LegN)]\text{-}BSA\}(PF_6)_2$ conjugate | Emission Intensity (arbitrary units) $\{[Ru(bpy)_2(LegS)]\text{-}IgG\}(PF_6)_2$ conjugate |
|---|---|---|
| 0 | 32.53 | 24.33 |
| $10^{-11}$ M | 68.25 | 56.46 |
| $10^{-10}$ M | 109.63 | 85.28 |
| $10^{-9}$ M | 201.22 | 161.86 |
| $10^{-8}$ M | 598.12 | 403.74 |

EXAMPLE 10

Analytical Method for Detecting Troponine I (TnI) in Serum

As an example of an analytical method in which an ECL complex according to the present invention is employed, an electrochemiluminescent immunochemical sandwich assay is described for the detection of Troponine I (TnI) in serum. In this type of assay, two monoclonal antibodies which are specific for two different epitopes of the analyte TnI, are used. The analytical scheme of the assay is as follows: the first anti-TnI Mab$_1$ antibody is used as a capture antibody and is conjugated with biotine, the second anti-TnI Mab$_2$ antibody is conjugated with the ECL complex [Ru(bpy)$_2$(LegS)]PF$_6$)$_2$ according to a procedure similar to that of Example 6.

The immunologic reaction between the analyte and the monoclonal antibody pair takes place in homogeneous phase, in the presence of a solid phase, for example a gold electrode coated with streptavidine, that constitutes the free/bound separation means.

In summary:

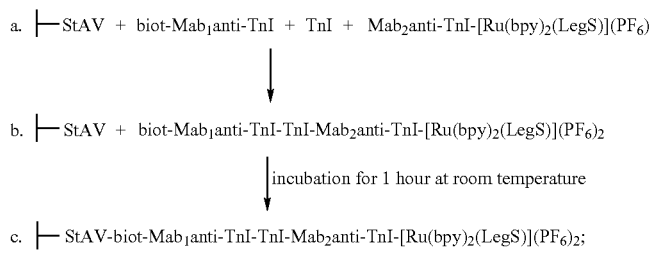

wherein:

I-STAV is the gold electrode coated with streptavidine, biot-Mab$_1$anti-TnI is the capture antibody conjugated with biotin, TnI is Troponine I and Mab$_2$anti-TnI-[Ru(bpy)$_2$(LegS)](PF$_6$)$_2$ is the antibody conjugated with the ECL synthesized in Example 3. After washing the electrode with a suitable washing buffer, a number of Mab$_2$anti-TnI—[Ru(bpy)$_2$(LegS)](PF$_6$)$_2$ molecules equal to that of the analyte will remain anchored to the solid phase. This allows for the calculation of the analyte concentration in the starting serum, through the construction of a titration curve with calibrators having a known concentration of TnI. Detection is performed using a device analogous to that described in Example 8, wherein the glassy carbon working electrode is replaced by a gold electrode coated with streptavidine. Table 4 summarizes the results obtained:

TABLE 4

| Troponine I concentration ng/ml | Emission intensity (arbitrary units) |
|---|---|
| 0 | 30.52 |
| 5 | 41.26 |
| 20 | 69.35 |
| 40 | 115.22 |
| 100 | 236.42 |
| 200 | 408.87 |
| 400 | 775.74 |

The invention claimed is:

1. A compound having the following general formula (I), including the valence tautomers thereof:

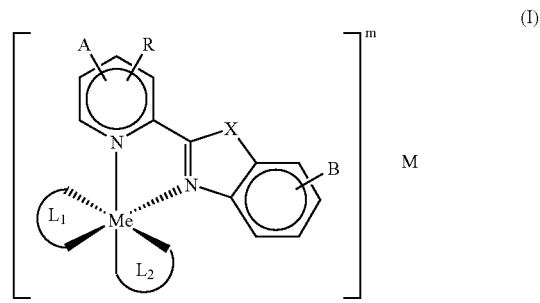

wherein:

Me is a transition metal or a rare earth metal;

R is a functional group selected from the group consisting of —COOH, —OH, and —NH$_2$, or is —R$_{10}$—Y wherein R$_{10}$ is a saturated or unsaturated, linear or branched alkyl chain having from 1 to 30 carbon atoms, in which one or more carbon atoms are optionally each replaced by a heteroatom independently selected from the group consisting of oxygen and sulphur, or by a —NH— group, a —CONH— group, or an aromatic or non-aromatic, 4-, 5- or 6-membered cyclic grouping of carbon atoms, in which one or more carbon atoms are optionally each replaced by a heteroatom independently selected from the group consisting of oxygen, sulphur, nitrogen and selenium, and wherein Y is selected from the group consisting of hydrogen, carboxyl, carbonyl, amino, sulphidryl, thiocyanate, isothiocyanate, isocyanate, maleimide, hydroxyl, phosphoramidite, glycidyl, imidazolyl, carbamoyl, anhydride, bromoacetamido, chloracetamido, iodoacetamido, sulphonyl halide, acyl halide, aryl halide, hydrazide, N-hydroxysuccinimidyl ester, N-hydroxysulphosuccinimidyl ester, phtalimide ester, naphtalimide ester, hydrazine, aldehyde, —C≡CH and —COZ wherein Z is a leaving group;

A and B are independently of each other:

from zero to 4 substituents independently selected from the group consisting of hydrogen, —COOH, —OH, —NO$_2$, —OCH$_3$, —SO$_3$H, —SO$_3^-$, —R$_{10}$—Y and —COZ;

a 5- or 6-membered homocyclic or heterocyclic condensed ring optionally substituted with one to 4 substituents independently selected from the group consisting of hydrogen, —SO$_3^-$, —SO$_3$H, —COOH, —OH, —NO$_2$, —OCH$_3$, —NH$_2$, carbonyl (—CHO), thiocyanate (—SON), isothiocyanate (—CNS), epoxy, —R$_{10}$—Y and —COZ; or a homocyclic or heterocyclic condensed 2-fused-ring system, having 5 or 6 atoms in each ring, optionally substituted with one to 4 substituents selected from the group consisting of hydrogen, —SO$_3^-$, —SO$_3$H, —COOH, —OH, —NO$_2$, —OCH$_3$, —NH$_2$, carbonyl (—CHO), thiocyanate (—SCN), isothiocyanate (—CNS), epoxy, —R$_{10}$—Y, and —COZ;

X is selected from the group consisting of —O—, —S—, —Se—, —NH—, —C(CH$_3$)$_2$—, —NR$_{100}$— and

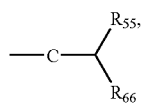

wherein R$_{100}$ is selected from the group consisting of hydrogen and —R$_{10}$—Y, and R$_{55}$ and R$_{66}$ are independently of each other a saturated or unsaturated, linear or branched alkyl chain having from 1 to 30 carbon atoms, in which one or more carbon atoms are optionally each replaced by a heteroatom independently selected from the group consisting of oxygen and sulphur, or by a —NH— group, a —CONH— group, or an aromatic or non-aromatic, 4-, 5- or 6-membered cyclic grouping of carbon atoms, in which one or more carbon atoms are optionally each replaced by a heteroatom independently selected from the group consisting of oxygen, sulphur, nitrogen, and selenium;

M is a counter ion; m is a number between −5 and +5;

L$_1$ and L$_2$ are independently of each other a bidentate ligand selected from the group consisting of:

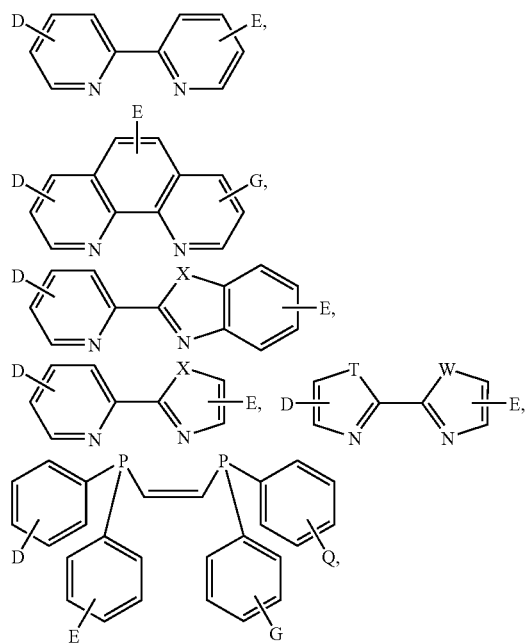

wherein D, E, G and Q have each independently the meanings previously defined for A and B, and T and W have each independently the meanings previously defined for X.

2. A compound according to claim 1, wherein the Z leaving groups are independently of each other selected from the group consisting of —Cl, —Br, —I, —OH, —OR$_{22}$, —OCOR$_{22}$, wherein R$_{22}$ is linear or branched C$_1$-C$_4$ alkyl, —O—CO—Ar, wherein Ar is optionally substituted aryl, —O—CO-Het, wherein Het is a heterocyclic system, and —NR$_{33}$R$_{44}$, wherein R$_{33}$ and R$_{44}$ are each independently linear or branched C$_1$-C$_{10}$ alkyl.

3. A compound according to claim 1 or 2, wherein Me is selected from the group consisting of ruthenium, osmium, iridium, rhenium, and chromium.

4. A compound selected from the group consisting of:

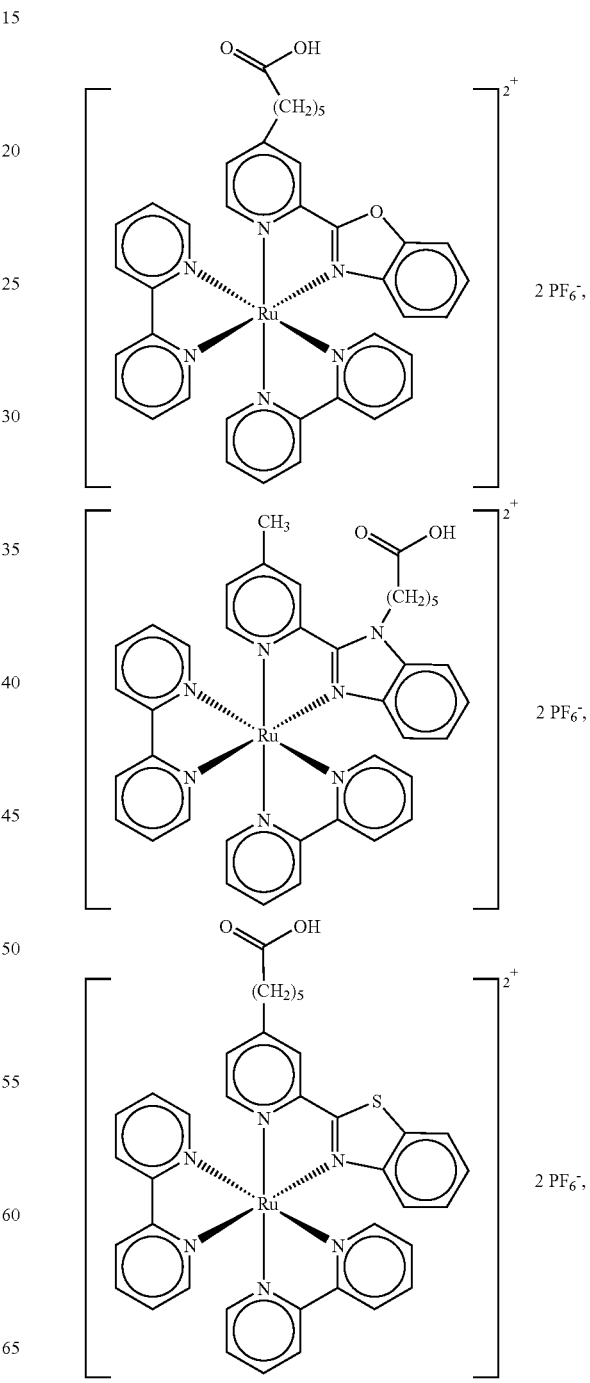

-continued

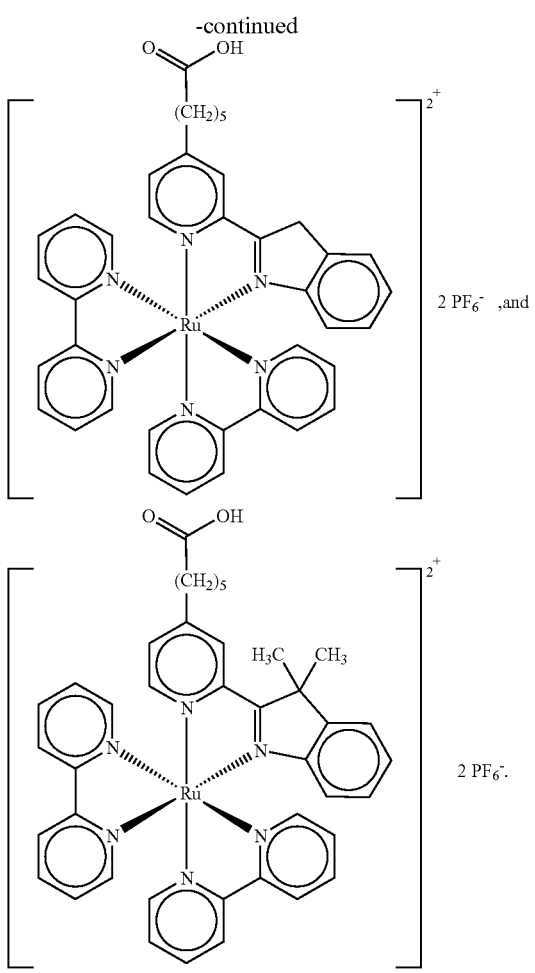

5. A method of producing a compound according to claim 1, comprising reacting a pyridylbenz-X-azolic ligand of formula (A)

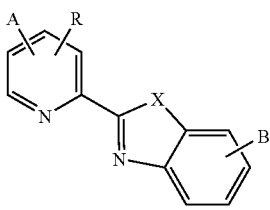

with a compound of formula Me(L1)(L2)Alg, wherein X, A, R, B, L1 and L2 are as previously defined and Alg is halogen.

6. A conjugate with the formula α-$\omega_1$, wherein α is a compound according to claims 1 and $\omega_1$ is a biological substance containing a free amino group or a free —SH group.

7. A conjugate according to claim 6, wherein ω1 is selected from the group consisting of proteins, lipoproteins, glycoproteins, peptides, polypeptides, nucleic acids, oligonucleotides, nucleotides, DNA probes, oligosaccharides, polysaccharides, lipopolysaccharides, hormones, alcaloids, steroids, vitamins, amino acids, sugars, antibodies, antigens, haptens, and fragments thereof.

8. A conjugate of formula α-$\omega_2$, wherein α is a compound according to claim 1; and $\omega_2$ is a fluorescent dye selected from the group consisting of a cyanine and an indocyanine, which is capable of absorbing at wavelengths at which the α compound is able to emit.

9. A conjugate of formula α($\omega_1$)($\omega_2$), wherein α is a compound according to claim 1; $\omega_1$ is a biological substance selected from the group consisting of proteins, lipoproteins, glycoproteins, peptides, polypeptides, nucleic acids, oligonucleotides, nucleotides, DNA probes, oligosaccharides, polysaccharides, lipopolysaccharides, hormones, alcaloids, steroids, vitamins, amino acids, sugars, antibodies, antigens, haptens, and fragments thereof; and $\omega_2$ is a fluorescent dye selected from the group consisting of a cyanine and an indocyanine.

10. An analytical method for the detection of an analyte in a sample, comprising the following steps:
(i) to contact the sample with a conjugate according to claim 6, in suitable conditions for the binding of the conjugate to the analyte, if present; and
(ii) to assess the presence or the quantity of analyte bound to the conjugate in the sample by measuring the luminescence emitted by the conjugate bound to the analyte.

11. The method according to claim 10, wherein the analyte is separated from the other sample components before the contact with the conjugate.

12. The method according to claim 10, wherein ω1 is an antibody.

13. The method according to claim 12, wherein the analyte is separated from the other sample components by contacting with a second antibody attached to a solid phase.

14. The method according to claim 10, wherein ω1 is a DNA probe.

15. The method according to claim 14, wherein the analyte is separated from the other sample components by contacting with a second DNA probe attached to a solid phase.

16. A compound according to claim 2, wherein $R_{22}$ is selected from the group consisting of methyl, ethyl, t-butyl, and i-propyl.

17. A compound according to claim 2, wherein Het is a heterocyclic system selected from the group consisting of succinimide, sulphosuccinimide, phtalimide, and naphtalimide.

18. A conjugate with the formula α-$\omega_1$, wherein α is a compound according to claim 4 and $\omega_1$ is a biological substance containing a free amino group or a free —SH group.

19. A conjugate according to claim 18, wherein ω1 is selected from the group consisting of proteins, lipoproteins, glycoproteins, peptides, polypeptides, nucleic acids, oligonucleotides, nucleotides, DNA probes, oligosaccharides, polysaccharides, lipopolysaccharides, hormones, alcaloids, steroids, vitamins, amino acids, sugars, antibodies, antigens, haptens, and fragments thereof.

20. A conjugate of formula α-$\omega_2$, wherein α is a compound according to claim 4; and $\omega_2$ is a fluorescent dye selected from the group consisting of a cyanine and an indocyanine, which is capable of absorbing at wavelengths at which the α compound is able to emit.

21. A conjugate of formula α($\omega_1$)($\omega_2$), wherein α is a compound according to claim 4; $\omega_1$ is a biological substance selected from the group consisting of proteins, lipoproteins, glycoproteins, peptides, polypeptides, nucleic acids, oligonucleotides, nucleotides, DNA probes, oligosaccharides, polysaccharides, lipopolysaccharides, hormones, alcaloids, steroids, vitamins, amino acids, sugars, antibodies, antigens, haptens, and fragments thereof; and $\omega_2$ is a fluorescent dye selected from the group consisting of a cyanine and an indocyanin.

22. An analytical method for the detection of an analyte in a sample, comprising the following steps:
   (i) to contact the sample with a conjugate according to claim 18, in suitable conditions for the binding of the conjugate to the analyte, if present; and
   (ii) to assess the presence or the quantity of analyte bound to the conjugate in the sample by measuring the luminescence emitted by the conjugate bound to the analyte.

23. The method according to claim 22, wherein the analyte is separated from the other sample components before the contact with the conjugate.

* * * * *